(12) United States Patent
Menke et al.

(10) Patent No.: US 7,919,000 B2
(45) Date of Patent: Apr. 5, 2011

(54) REACTOR COMPRISING A SUPPLY DISTRIBUTION SYSTEM FOR ANAEROBIC WASTE WATER TREATMENT

(75) Inventors: Lukas Menke, Munich (DE); Georgios Troubounis, Munich (DE); Ulrich Knoerle, Waldburg (DE); Dieter Efinger, Kumhausen (DE)

(73) Assignees: Aquatyx Wassertechnik GmbH, Ravensburg (DE); Meri Entsorgungstechnik Fuer die Papierindustrie GmbH, München (DE)

( * ) Notice: Subject to any disclaimer, the term of this patent is extended or adjusted under 35 U.S.C. 154(b) by 123 days.

(21) Appl. No.: 12/373,465

(22) PCT Filed: Jul. 12, 2007

(86) PCT No.: PCT/EP2007/006216
§ 371 (c)(1),
(2), (4) Date: May 15, 2009

(87) PCT Pub. No.: WO2008/006596
PCT Pub. Date: Jan. 17, 2008

(65) Prior Publication Data
US 2010/0000940 A1    Jan. 7, 2010

(30) Foreign Application Priority Data

Jul. 13, 2006  (DE) .................. 10 2006 032 489
Sep. 8, 2006  (DE) .................. 20 2006 013 811 U (51) Int. Cl.
*C02F 3/28* (2006.01)
(52) U.S. Cl. ............... 210/603; 210/512.1; 210/928
(58) Field of Classification Search .......... 210/601, 210/603, 150, 512.1, 928
See application file for complete search history.

(56) References Cited

U.S. PATENT DOCUMENTS

| 3,527,575 A | 9/1970 | Thompson |
| 4,726,899 A | 2/1988 | Stafford et al. |
| 5,409,610 A * | 4/1995 | Clark ...................... 210/603 |

(Continued)

FOREIGN PATENT DOCUMENTS
DE    1667058    6/1971
(Continued)

OTHER PUBLICATIONS
English language Abstract of EP 0493727 A1 (Jul. 8, 1992).
(Continued)

*Primary Examiner* — Fred Prince
(74) *Attorney, Agent, or Firm* — Greenblum & Bernstein, P.L.C.

(57) ABSTRACT

Disclosed is a reactor for anaerobically treating waste water, especially treating waste water from the paper industry. Said reactor comprises a reactor vessel, at least one supply pipe which is arranged in the bottom area of the reactor vessel and is used for feeding waste water that is to be treated into the reactor, at least one supply distributor for mixing the waste water fed to the reactor with the medium located in the reactor, at least one overflow port which is disposed on the top reactor vessel and is used for discharging treated water, and at least one separator. The supply distributor is provided with at least one deflection means that is embodied such that waste water discharged from the at least one supply pipe is diverted into a circular current from the perspective of the cross-section of the reactor, one to 80 percent of the cross-section of the reactor being filled by the at least one deflection means. The invention further relates to a method for anaerobically treating waste water.

18 Claims, 6 Drawing Sheets

U.S. PATENT DOCUMENTS

| | | | |
|---|---|---|---|
| 2003/0038079 A1* | 2/2003 | Miller, III | 210/603 |
| 2006/0065593 A1 | 3/2006 | Hansen et al. | |

FOREIGN PATENT DOCUMENTS

| | | |
|---|---|---|
| DE | 4042223 A1 | 7/1992 |
| DE | 4208148 A1 | 9/1992 |
| DE | 19815616 A1 | 10/1999 |
| DE | 10358400 A1 | 7/2005 |
| EP | 153299 A1 | 8/1985 |
| EP | 170332 A1 | 2/1986 |
| EP | 0493727 A1 | 7/1992 |
| EP | 539430 B1 | 10/1994 |
| EP | 0948463 B1 | 1/2001 |
| EP | 1071636 B1 | 1/2002 |
| EP | 1553058 A1 | 7/2005 |
| EP | 1609763 A1 | 12/2005 |
| WO | 2004/035486 A1 | 4/2004 |
| WO | 2006/132523 A1 | 12/2006 |

OTHER PUBLICATIONS

English language Abstract of DE 10358400 A1 (Jul. 7, 2005).
English language Abstract of EP 1609763 A1 (Dec. 28, 2005).

* cited by examiner

REACTOR COMPRISING A SUPPLY DISTRIBUTION SYSTEM FOR ANAEROBIC WASTE WATER TREATMENT

The present invention relates to a reactor for the anaerobic treatment of waste water, in particular of waste water from the paper industry, comprising a reactor tank, at least one supply line arranged in the lower region of the reactor tank for the supply of waste water to be treated into the reactor, at least one supply distributor for the mixing of the waste water supplied to the reactor with the medium located in the reactor, at least one overflow arranged at the upper region of the reactor tank for the draining of treated water and at least one separator.

A plurality of mechanical, chemical and biological processes and corresponding reactors are known for waste water treatment. In biological waste water treatment, the waste water to be treated is contacted with aerobic or anaerobic microorganisms which degrade the organic impurities contained in the waste water primarily to carbon dioxide, biomass and water in the case of aerobic microorganisms and primarily to carbon dioxide and methane and only in a low proportion to biomass in the case of anaerobic microorganisms. In this respect, the biological waste water treatment methods have increasingly been carried out using anaerobic microorganisms in very recent times because in anaerobic waste water treatment oxygen does not have to be introduced into the bioreactor under a high energy effort, biogas rich in energy is produced in the treatment which can subsequently be used to gain energy and much smaller amounts of excess sludge are produced. Depending on the kind and form of the biomass used, the reactors for anaerobic waste water treatment are divided into contact sludge reactors, UASB reactors, EGSB reactors, fixed bed reactors and fluidized bed reactors. Whereas the microorganisms in fixed bed reactors adhere to stationary carrier materials and the microorganisms in fluidized bed reactors adhere to freely movable small carrier material, the microorganisms in the UASB and EGSB reactors are used in the form of so-called pellets. In contrast to UASB (upflow anaerobic sludge blanket) reactors, ESBG (expanded granular sludge bed) reactors are higher and have a much smaller base surface with the same volume.

With UASB reactors and EGSB reactors, waste water to be treated or a mixture of waste water to be treated and already treated waste water from the outflow of the anaerobic reactor (hereinafter the "reactor inflow") is supplied continuously to the reactor via an inflow in the lower reactor region and is guided through a sludge bed located above the inflow and containing microorganism pellets. On the degradation of the organic compounds from the waste water, the microorganisms in particular form gas which contains methane and carbon dioxide (which is also called biogas) of which some accumulates at the microorganism pellets in the form of small bubbles and of which some rises upward in the reactor in the form of free gas bubbles. The specific weight of the pellets falls due to the accumulated gas bubbles so that the pellets rise upward in the reactor. To separate the biogas formed and the rising pellets from the water, separators are arranged in the middle and/or upper parts of the reactor, usually in the form of gas hoods under whose crowns biogas collects which forms a gas cushion under which a flotation layer of microorganism pellets and waste water is located. Treated water liberated from gas and microorganism pellets rises upwardly in the reactor and is drained off via overflows at the upper end of the reactor. Such methods and corresponding reactors are described, for example, in EP 0 170 332 A1 and in EP 1 071 636 B1.

The uniform distribution of the waste water supplied to the reactor via the inflow over the reactor cross-section is particularly important in the previously described methods to achieve a good mixing of the sludge pellets located in the reactor, of the water located in the reactor and of the added waste water. To satisfy these demands, a plurality of reactors equipped with corresponding inflow distributors has already been proposed.

A bioreactor having a reactor tank is known from EP 0 539 430 B1 which has an inflow inlet system comprising at least one inflow line at the lower end of the reactor tank, said inflow inlet system being separated by a substantially conically arranged partition from the reaction chamber containing the microorganisms, with the partition extending over the total reactor cross-section. In this connection, the outflow openings of the inflow lines are aligned at least partly tangentially and at least one radial slot is provided at the partition and is formed by two radial edges which overlap one another at a specific vertical spacing, with the at least one radial slot forming a connection between the inflow inlet chamber and the reaction chamber. A circular flow of the inflow water with respect to the longitudinal axis of the reactor should be achieved by the orientation of the outflow opening(s) of the inflow line(s) and of the at least one radial slot and an infiltration of solids into the inflow inlet system should be prevented, in particular after switching off the reactor, by the arrangement of the radial slots. However, this reactor and the process operated therewith have a plurality of disadvantages.

Solids contained in the supplied waste water collect inside the inflow inlet system and do not reach the reaction chamber due to the partition between the inflow inlet system and the reactor chamber filling 100% of the cross-section of the reactor. However, solid deposited in the inflow inlet system, that is beneath the conical partition, can only be removed from the reactor with difficulty. In addition, the reactor must be switched off for a removal of the solids from the inflow inlet system. On the other hand, lime crystallizes at the pellets in the reactor chamber, in particular with waste water to be treated having a high lime content, so that some of the microorganism sludge pellets at which the lime crystallizes have a high specific weight so that these pellets sediment in the reactor and are deposited at the lower end of the conical partition in the region of the reactor wall. These sediments can also only be removed from the reactor with a very high effort and/or cost. In addition, the effective diameter of the reactor is reduced by the sediment at the reactor wall so that the effective reaction volume is reduced. Furthermore, the radial slots are blocked or clogged by the sediments as the operating time of the reactor increases which results in a large pressure increase in the distributor system. This can have the result that the water level rises significantly in the gas separator, so that congestion can arise in the gas separator, which can result in the necessity of switching off the inflow. Because additionally carbon dioxide is separated in the gas separator, the pH rises significantly in the waste water return line, which results in a precipitation of lime in the inflow region so that the precipitate has to be removed at a high cost after the reactor has been switched off. For these reasons, the aforesaid reactor for the treatment of waste water with a high lime content, such as waste water from the paper industry which can simultaneously also contain sedimentable impurities in the form of paper fillers and the like, is in need of improvement.

It is the object of the present invention to provide a reactor with an inflow distributor with which the aforesaid disadvantages can be avoided. The reactor should in particular be suitable for the treatment of waste water with constituents tending to be precipitated in the anaerobic treatment, such as lime, in particular for the treatment of waste water from the paper industry and should permit a uniform distribution of the inflow over the total reactor cross-section and an ideal fluidization of the sludge bed. In addition, clogging in the inflow region, in particular in the region of the inflow distributor, should be reliably avoided and an accumulation of solids in the region of the inflow distributor, in particular the formation of dead spots due to solid sediments, should be reliably prevented.

A reactor is known for anaerobic treatment of waste water from US 2006/0065593 A1 which comprises a reactor tank, at least one inflow line, at least one overflow as well as a separator, with a T-piece being arranged at the outlet opening of the inflow line and with a distribution plate provided in the lower region of the reactor.

A reactor for anaerobic treatment of organic substrates is described in EP 0 153 299 A1 which comprises an inflow line, a buffer zone, a distribution space and a reaction space separated from the distribution space by an intermediate ceiling, with the buffer zone being made as a hollow cylinder which is arranged concentrically around the longitudinal axis of the reactor and at whose lower end distribution wings are provided and with the inflow line opening into the upper region of the buffer zone.

This object is satisfied in accordance with the invention by a reactor having the features of claim 1 and in particular by a reactor for the anaerobic treatment of waste water, comprising a reactor tank, at least one inflow line arranged in the lower region of the reactor tank for the supply of waste water to be treated into the reactor, at least one inflow distributor for the mixing of the waste water supplied to the reactor or of recycled material with the medium located in the reactor, at least one overflow arranged at the upper region of the reactor tank for the drainage of treated water, as well as at least one separator, with the inflow distributor comprising at lest one deflection means, with the at least one deflection means being designed such that waste water emerging from the at least one inflow line is deflected into a circular flow, viewed from the reactor cross-section, and with 1 to 80% of the reactor cross-section being filled by the at least one deflection means or by the inflow distributor.

An exceptional mixing of the waste water supplied to the reactor with the medium located in the reactor is made possible by the inflow distributor comprising at least one deflection means and the design of the at least one deflection mean such that waste water emerging from the outlet opening of the at least one inflow line is deflected into a circular flow viewed from the reactor cross-section. Furthermore, the flow guidance of the inflow waste water effected by the at least one deflection means enables a uniform distribution of the inflow water over the total reactor cross-section. Since the at least one deflection means or the inflow distributor fills up less than 80% of the reactor cross-section, a complete division of the reactor into two separate zones, namely into an inflow inlet system and a reaction chamber arranged thereabove, is avoided so that, on the one hand, solids contained in the inflow do not collect in the region of the inflow distributor, but rather flow upwardly due to the upwardly directed flow in the reactor and, on the other hand, sediments sinking downwardly from the upper reactor region do not sediment in the region of the inflow distributor, but are rather directly conducted into a zone from which they can be removed simultaneously from the reactor during the ongoing process. The formation of dead spots which reduce the effective reactor cross-section are thus in particular avoided. A pressure increase in the distributor system can thus in particular also be reliably avoided so that an increase in the water level in the gas separator is avoided. As a result of this, the reactor in accordance with the invention is in particular suitable for the anaerobic treatment of waste water charged with solids and in particular for the anaerobic treatment of waste water from the paper industry which has sedimentable impurities as well as a high content of dissolved lime.

The at least one deflection means or the inflow distributor preferably fills 2 to 70%, particularly preferably 3 to 60% and very particularly preferably 5 to 50% of the reactor cross-section. In the sense of the present invention, this is understood such that the integral of the portion of the singular or plural deflection means amounts/amount to 2 to 70% or 3 to 60% or 5 to 50% at every cross-sectional surface of the reactor. Since the at least one deflection means fills up at least 2% or 3% or 5% of the reactor cross-section, it is achieved that the reactor inflow is deflected into a stable circular flow viewed from the reactor cross-section so that an excellent mixing of the reactor inflow with the medium located in the reactor is achieved. It is moreover achieved by the filling of a maximum of 80% or 70% or 60% or 50% of the reactor cross-section by the singular or plural deflection means that solids contained in the supplied waste water rise into the region of the sludge pellet zone of the reactor due to the circular, upwardly directed water flow (spiral flow) and, on the other hand, solid sinking down from the upper reactor region with a high specific density does not collect in the region of the inflow distributor, but rather sinks down onto the reactor base and can be removed from the reactor from there during the ongoing process.

In a further development of the idea of the invention it is proposed to let the at least one inflow line end outside the reactor tank and to provide at least one slot in the wall of the lower region of the reactor tank, with the waste water emerging from the at least one inflow line entering through said at least one slot into the lower region of the reactor tank. This embodiment is simple in construction, on the one hand, because devices for the passage of the inflow line through the reactor tank can be dispensed with and, on the other hand, it allows the deflection means to be arranged directly in the region of the reactor tank. Since the at least one slot is provided in the reactor wall, a partition wall in the reactor, in particular a partition wall in the reactor filling the total reactor cross-section and having the aforesaid disadvantages, can be dispensed with.

In accordance with a preferred embodiment of the present invention, at least one deflection means is provided in the interior of the reactor in the region of the at least one slot and is made such that the waste water entering into the reactor from the at least one slot is deflected into a circular flow, viewed from the reactor cross-section. This embodiment allows an effective deflection of the waste water supplied to the reactor into a circular flow, viewed from the reactor cross-section, with a design of the inflow distributor which is simple in construction.

To achieve a particularly effective deflection of the waste water supplied to the reactor into a circular flow, it is proposed in a further development of the idea of the invention to arrange the at least one deflection means such that it covers or overlaps at least one slot at least partly.

It is in particular preferred for the achieving of the aforesaid purpose if the at least one deflection means covering or overlapping the at least one slot at least partly substantially has the same base shape as the at least one slot.

Generally, both the at least one slot and the at least one deflection means can have any desired geometry, with polygonal, circular, elliptical, oval, square and rectangular base shapes being named only by way of example. The at least one slot and the at least one deflection means preferably have the same base shape, with particularly good results being achieved when the base shape of both the at least one slot and of the at least one deflection means is at least substantially rectangular.

To be able to dispense with separate fastening devices for the at least one deflection means, the at least one deflection means is preferably connected at one of its sides to a side of the at least one slot. This can be realized in a particularly simple manner from a construction aspect if both the at least one slot and the at least one deflection means have a substantially rectangular base shape and the longitudinal side or wide side of the at least one deflection means is connected to the longitudinal side or wide side of the at least one slot.

In order to achieve an effective deflection of the reactor inflow supplied to the reactor through the at least one slot into a circular flow and, on the other hand, to be able to close the at least one slot easily on the switching off of the reactor, it is preferred in accordance with a further preferred embodiment of the present invention that the at least one deflection means is rotatably connected to the at least one slot, for example via a hinge.

An effective deflection of the waste water supplied to the reactor interior through the at least one slot is in particular achieved when the at least one deflection means extends, viewed from the connection point of the at least one deflection means having the at least one slot, relative to the at least one slot, at an angle between 5° and 85°, preferably between 10° and 700, particularly preferably between 20° and 50° and very particularly preferably between 30° and 40°.

To avoid a deposition of solids located in the reactor medium at right angles of the reactor tank, it is preferred to make the lower part of the reactor tank conically converging downwardly. It is thereby achieved that solid sedimenting at the reactor tank wall sinks down to the lowest point of the reactor base and collects there. In this case, it has proven to be advantageous to provide the at least one slot in the conically converging part of the reactor tank and the at least one deflection means in the region of the at least one slot.

Alternatively to this, it is possible and also preferred to form the lower part of the reactor tank as a double cone, with the upper part of the double cone preferably having a smaller angle than the lower part of the double cone with respect to the horizontal plane and with the at least one slot preferably being provided in the upper part of the double cone. In this embodiment, the angle of the upper part of the double cone amounts, relative to the horizontal plane, preferably to between 20° and 50° and particularly preferably between 25° and 35° and the angle of the lower part of the double cone amounts, likewise relative to the horizontal plane, preferably to between 30° and 70° and particularly preferably between 40° and 50°.

In the aforesaid embodiment, the at least one slot is preferably provided in the upper part of the double cone of the reactor tank and the at least one deflection means is provided in the region of the at least one slot. It is thereby achieved that solid sedimenting at the reactor tank wall sinks down to the lowest point of the reactor base in the lower part of the double cone and collects there and a clogging of the at least one slot provided in the upper part of the double cone can thus be reliably prevented.

To achieve a stable circulation guidance of the reactor inflow, it has moreover proved to be advantageous to provide at least two slots in the lower region of the reactor tank. Since a plurality of deflection means are provided in the inflow distributor, it is possible to distribute the deflection means uniformly over the cross-section of the reactor so that a plurality of regions free of deflection means are present in the inflow distributor, with respect to the reactor cross-section, and the cross-sectional area of the individual deflection means is comparatively low. The number and the shape of the deflection means in the reactor depend inter alia on the cross-section of the reactor and on the quantity of the reactor inflow per time unit. With the dimensions usual for reactors for the anaerobic treatment of waste water, the number of the slots provided in the lower region of the reactor tank preferably amounts to between 5 and 200, particularly preferably between 25 and 150 and very particularly preferably between 50 and 75.

In a further development of the idea of the invention, it is proposed to arrange the individual slots in a row spaced apart from one another in the radial direction viewed from the longitudinal axis of the reactor and separated from one another by the reactor tank wall and to provide 2 to 50, preferably 5 to 30 and particularly preferably 5 to 15 such rows in the lower region of the reactor tank. This, on the one hand, allows the collecting together of the waste water supply to the individual slots of a row in the form of a collection line and, on the other hand, the control of the waste water supply to the slots of different rows independently of one another.

The individual slots and/or the at least one deflection means are preferably distributed in surface proportionality viewed radially outwardly from the longitudinal axis of the reactor. This can be achieved, for example, in that, viewed in the radial direction from the longitudinal axis of the reactor, an equal number of slots or deflection means are provided on each circle area imagined concentrically around the longitudinal axis of the reactor, but the individual slots or deflection means have a larger dimension with an increasing radial direction. Furthermore, this can particularly preferably be achieved in that the individual slots or the individual deflection means each have the same size, but that, viewed in the radial direction from the longitudinal axis of the reactor, more slots or deflection means are arranged per circular area imagined concentrically around the longitudinal axis of the reactor as the spacing from the longitudinal axis of the reactor increases.

It is preferred for this reason to provide a respective collection line, which is respectively connected to one inflow line, beneath each row of slots for the supply into the reactor via the slots of the waste water to be treated. In this respect, the collection lines can have any desired geometrical shape, in particular, viewed in cross-section, a U-section, V-section or rectangular section. Alternatively to this, the collection lies can also be provided in the form of a half-pipe. The collection lines can preferably be made with a non-constant cross-section. The cross-sectional change is particularly preferably selected so that the emergence speed of the reactor inflow in an embodiment of the collection line having at least two slots has the same respective speed through the slot into the reaction space.

To achieve an effective deflection of the reactor inflow supplied through the slots, the number of the individual deflection means and the dimensions of the individual deflection means are preferably selected so that 3 to 50%, preferably 5 to 40% and particularly preferably 10 to 20% of the reactor cross-section is filled by the singular or plural deflection means.

In accordance with a further preferred embodiment of the present invention, provision is made to provide at least one deflection means designed as a planar, multi-arm spiral in addition to the previously described slots and singular or plural deflection means or alternatively to the previously described slots and singular or plural deflection means in the reactor. A deflection of the waste water supplied to the reactor into a circular flow can be achieved particularly simply and reliably by a planar, multi-arm spiral design of the at least one deflection means.

In the sense of the present invention, a planar multi-arm spiral is understood as any planar spiral which includes at least two spiral arms, and indeed independently of the specific shape of the spiral arms and independently of their lengths. This term in particular also includes spirals whose individual spiral arms surround the center of the spiral at an angle of less than 360° or less than 180°.

Particularly good results are in particular obtained when the at least one spiral deflection means has at least four spiral arms and particularly preferably between four and eight spiral arms. An effective deflection of the waste water supplied to the reactor into a circular flow is thereby achieved.

The present invention is generally not restricted to the specific shape of the individual spiral arms of the deflection means, with good results in particular being achieved with spiral deflection means whose individual spiral arms substantially have the shape of a semi-ellipse. In the last-named variant, the curvature of individual spiral arms or of all spiral arms preferably extends in the same direction.

To achieve a particularly effective deflection of the waste water supplied to the reactor, it is proposed in a further development of the idea of the invention to design the at least one spiral deflection means such that it includes four to eight substantially semi-elliptical or semi-circular spiral arms of which preferably two to four spiral arms have a different length to the rest of the spiral arms. It is thereby achieved that the waste water is supplied to the reactor uniformly, viewed over the cross-section of the reactor. An example for a particularly suitable design of this embodiment of the aforesaid invention is a deflection means having eight substantially semi-elliptical or semi-circular spiral arms of which four spiral arms have a different length to the other four spiral arms.

To keep the construction effort small and to ensure a uniform water passage through the spiral deflection means, it is proposed in a further development of the idea of the invention to provide a distribution device at the center of the spiral deflection means, with the inflow line at the center of the one deflection means opening into the distribution device and the waste water guided through the inflow line being distributed onto the individual spiral arms of the deflection means via the distribution device.

The spiral arms of the deflection means preferably have a tubular cross-section. In this embodiment of the present invention, the individual spiral arms of the deflection means are accordingly completely sheathed, viewed over the radial section, so that a penetration of solids into the spiral arms can be reliably prevented since the only opening of the spiral arms, i.e. the outlet opening of the spiral arms, is not accessible for solids from the interior of the reactor due to the liquid flowing out there.

In accordance with a further preferred alternative embodiment of the present invention, it is proposed to design the spiral arms of the deflection means hollow at the inside and open downwardly. In this case, an effective deflection of the liquid guided by the deflection means is achieved by the peripheral surfaces of the inwardly hollow and downwardly open spiral arms. In this embodiment, the outlet opening(s) of the inflow lines(s) associated with the individual spiral arms of the deflection means is/are preferably oriented into the inner hollow space of the spiral arms and particularly preferably tangentially to an imagined circle extending concentrically around the longitudinal axis of the reactor so that the water emerging from the outlet opening(s) of the inflow line (s) impacts on the inner peripheral surface of the spiral arms and is thereby deflected accordingly. In this respect, a circular deflection of the water supplied to the reactor is in particular reliably achieved when the spiral deflection means is arranged perpendicular to the longitudinal axis of the reactor and concentrically around the longitudinal axis of the reactor.

In the aforesaid embodiment, the spiral arms of the deflection means are preferably designed in the radial section as inversely V-shaped, inversely U-shaped, rectangular, trapezoidal or polygonal. It is in particular achieved by the inversely V-shaped design and the inversely U-shaped design of the spiral arms in the radial section that solids falling down onto the deflection means from above cannot collect on the periphery of the spiral arms, but rather slide off over the peripheral surface of the spiral arms and sink further downwardly in the reactor until they reach the lowest point of the reactor.

Alternatively to this, the spiral arms of the at least one spiral deflection means can also be designed as circular in radial section, with the lower part of the circular radial section being open and a respective one chamfer facing away from the spiral arms being applied at the two opening ends in radial section, with consequently the spiral arms of the at least one spiral deflection means having a substantially keyhole-like radial section. It is thereby achieved on the one hand that solids sinking onto the deflection means from above fall off the peripheral surface of the spiral arms and sink further downwardly in the reactor and it is prevented, on the other hand, that solids can penetrate into the hollow space of the spiral arms through a side flow from below and can be deposited there.

Another alternative is to design the spiral arms of the at least one spiral deflection means in diamond shape in radial section, with the lower parts of the diamond-shaped radial sections being open and a chamfer being applied to one of the two opening ends or to both opening ends of the individual radial sections of the spiral arms, said chamfer preferably being arranged leading outwardly from the spiral arms. It is hereby also reliably avoided that solids falling from above in the reactor onto the deflection means collect on the deflection means and that solids can penetrate from below into the hollow space of the spiral arms of the deflection means.

Alternatively to this, the spiral arms of the at least one spiral deflection means can also have any other known geometrical shape in radial section as long as it is ensured by the design of the spiral arms that no solids can enter into the hollow space of the spiral arms or that solids can collect upwardly on the peripheral surfaces of the spiral arms.

In order, on the one hand, to achieve an effective deflection of the waste water supplied to the reactor and, on the other hand, to avoid a sedimentation of solids sinking down in the reactor on the deflection means, it is proposed in a further development of the idea of the invention that 5 to 70%, preferably 10 to 60% and particularly preferably 20 to 50% of the reactor cross-section is filled by the at least one spiral deflection means.

The at least one spiral deflection means is preferably arranged perpendicular to the longitudinal axis of the reactor and concentrically around the longitudinal axis of the reactor. The deflection into a circular flow is promoted on the basis of this symmetrical arrangement.

In accordance with a further preferred embodiment of the present invention, it has proved to be advantageous to provide the lower part of the reactor in the form of a simple cone or of a double cone converging downwardly. It is thereby achieved that solids with high specific weights sinking down out of the upper reactor part sink down to the tip of the cone and can be drained off from there. A collection of sediments in the region of the inflow distributor, which results in the formation of dead spots and in a reduction of the effective reactor cross-section, can hereby be reliably avoided. This effect is amplified considerably by the spiral flow generated by the inflow distributor.

It is moreover preferred for the aforesaid reason to arrange a drain line at the lower end of the cone.

It is proposed in a further development of the idea of the invention to provide an inflow line in the lower region of the cone via which waste water, fresh water or the like can be introduced into the lower conical reactor region. A flushing of the reactor base can thereby take place as required. This is sensible, for example, when sediment was drawn out of the lower reactor region, to swirl up any sediment residues adhering to the lower reactor walls so that they sink down at the lowest point of the cone and can be drawn off out of the reactor via the drain line.

To be able to guide the microorganism pellets and the water contained in the reactor in the circuit, the reactor preferably has at least one sink line, particularly preferably a sink line arranged concentrically around the longitudinal axis of the reactor, or, provided that the reactor has two gas separators, two sink lines, with the upper end of the at least one sink line being connected to the gas separator(s) and with microorganism pellets and water separated in the gas separator(s) being able to be guided back into the lower reactor region via the lower outlet opening of the sink line(s). In this embodiment, the lower outlet opening of the at least one sink line is arranged above or in the region of the upper boundary of the at least one deflection means.

Provided that one or more sink lines are provided in the reactor, their lower outlet openings are preferably arranged tangentially to an imagined circle arranged concentrically around the longitudinal axis. When two or more sink lines are provided, these outlet openings can all be arranged in the same direction tangentially to an imaged circle arranged concentrically around the longitudinal axis, or alternatively to this, can be arranged alternately in opposite directions tangentially to an imaged circle arranged concentrically around the longitudinal axis.

However, the present invention is not restricted to reactors which have one or more sink lines. The reactor in accordance with the invention can rather also be operated without a sink line. In addition, the at least one sink line can also be arranged, with respect to the reactor cross-section, at any desired point. Finally, it is also possible to provide the at least one sink line outside the reactor tank. The at least one sink line can, for example, be arranged outside the reactor tank. Furthermore, at least one supply line can open into the sink line via which waste water to be treated, fresh water or a mixture thereof can be supplied to the sink line. The sink line preferably opens in the region of the inflow distributor in the reactor.

Due to the aforesaid properties and advantages of the reactor in accordance with the invention, it is in particular suitable as a UASB reactor or as an EGSB reactor.

In accordance with an alternative embodiment, the at least one deflection means preferably fills 20 to 70% and particularly preferably 30 to 60% of the reactor cross-section.

In this embodiment, the at least one deflection means is preferably made in ring shape since thereby a deflection of the waste water supplied to the reactor into a circular flow can be achieved particularly easily and reliably.

To achieve a stable circuit guidance of the water supplied to the reactor, it has moreover proven to be advantageous in this embodiment to provide at least two deflection means, particularly preferably two to five deflection means and very particularly preferably two or three deflection means, in the inflow distributor. It is thus possible to distribute the individual deflection means uniformly over the cross-section of the reactor so that a plurality of regions free of deflection means are present in the inflow distributor, with reference to the reactor cross-section, and the cross-sectional area of the individual deflection means is comparatively small. The specific number of deflection means in particular depends in this respect on the size of the reactor cross-section.

Ring-shaped is understood in the sense of the present invention not only as a circular ring, but rather generally a ring formed by a ring body which is thin in its radial section with respect to the total cross-section of the ring, with the base surface of the ring body being able to adopt any desired geometrical shape, for example, a circular, rectangular, oval, elliptical or polygonal shape.

With this embodiment, the ring body of the at least one ring-shaped deflection means can be inwardly hollow and downwardly open, with the outlet opening of the inflow line associated with the deflection means preferably being oriented into the inner hollow space of the ring body and particularly preferably tangentially to an imagined circle extending concentrically around the longitudinal axis of the reactor so that the water emerging from the outlet opening impacts onto the inner surface of the ring body and is thereby deflected accordingly. In this respect, a circular deflection of the water supplied to the reactor is in particular reliably achieved when the ring-shaped deflection means is arranged perpendicular to the longitudinal axis of the reactor and concentrically around the longitudinal axis of the reactor.

In this respect, the ring body of the at least one ring-shaped deflection means can be designed inversely V shaped, inversely U shaped, rectangular, trapezoidal or polygonal in radial section. Alternatively to this, the ring body of the least one ring-shaped deflection means can also be made circular in radial section, with the lower part of the circular radial section being open and with a respective chamfer extending away from the ring body being applied to the two opening ends in radial section, with consequently the ring body of the at least one ring-shaped deflection means having a substantially keyhole-like radial section. Another alternative is to design the ring body of the at least one ring-shaped deflection means in diamond shape in radial section, with the lower part of the diamond-shaped radial section being open and with a chamfer being applied to one of the two opening ends or to both opening ends which is preferably arranged leading outwardly away from the ring body.

Particularly good results are in particular obtained when the at least one ring-shaped deflection means has a round, an oval, an elliptical or a polygonal base area.

It is furthermore possible with this embodiment to arrange two identical or substantially like ring-shaped deflection means over one another. Two ring-shaped deflection means each having an inversely V-shaped radial section and a circular base surface can, for example, be arranged over one another so that a radial section in the form of a "double roof" results for this structure.

Alternatively to the at least one aforesaid ring-shaped deflection means, or in addition to the at least one aforesaid ring-shaped deflection means, the reactor in accordance with the invention can include at least one inwardly hollow deflection means made in hood shape, with the upper part of the hood being closed and the lower part of the hood being open. This deflection means is preferably also arranged perpendicular to the longitudinal axis of the reactor and concentrically around the longitudinal axis of the reactor. It is also possible that the at least one hood-shaped deflection means has the shape of a hollow cone, of a truncated hollow cone, a hollow semi-sphere or of a hollow truncated pyramid open at the base surface, but closed at the other surfaces. Good results are in particular obtained when the base surface of the hollow cone or of the hollow truncated cone is round, oval or elliptical or the base surface of the hollow truncated pyramid is polygonal, rectangular or square.

Alternatively to a ring-shaped and/or hood-shaped deflection means or in addition to a ring-shaped deflection means and/or hood-shaped deflection means, the reactor in accordance with the invention can have at least one deflection means which has the shape of a hollow truncated cone or of a hollow truncated pyramid open at the base surface and at the cover surface, but closed at the jacket surface. The deflection means is also preferably arranged perpendicular to the longitudinal axis of the reactor and concentrically around the longitudinal axis of the reactor with this aspect of the deflection means.

The number and the shape of the deflection means in the reactor depend inter alia on the cross-section of the reactor and on the quantity of the waste water supplied to the reactor per time unit. Whereas one deflection means can already be sufficient with smaller reactors, the number of the deflection means preferably amounts to between two and five and particularly preferably two or three with medium-sized and larger reactors.

The upper boundaries of all the deflection means included in the reactor are preferably substantially each arranged at the same level of the reactor.

A further subject of the present invention is a method for the anaerobic treatment of waste water, with waste water to be treated being supplied to a reactor comprising a reactor tank, at least one overflow arranged at the upper region of the reactor tank for the draining off of treated water, at least one separator, at least one inflow line arranged in the lower region of the reactor tank and having in each case at least one outlet opening for the supply of waste water to be treated into the reactor as well as at least one inflow distributor for the mixing of the waste water supplied to the reactor with the medium located in the reactor, with the inflow distributor comprising at least one deflection means of which 1 to 80% of the reactor cross-section is filled, with the outlet opening of the at least one inflow line being arranged such that the at least one deflection means is designed and the speed of the supplied waste water is set such that the waste water emerging from the outlet opening of the at least one inflow line being deflected in the inflow distributor into a circular flow, viewed from the reactor cross-section.

Particularly good results are in particular obtained when the method in accordance with the invention is carried out in a previously described reactor.

The present invention will be described in the following purely by way of example with reference to advantageous embodiments and to the enclosed drawings.

BRIEF DESCRIPTION OF THE DRAWINGS

There are shown.

Figure 1:
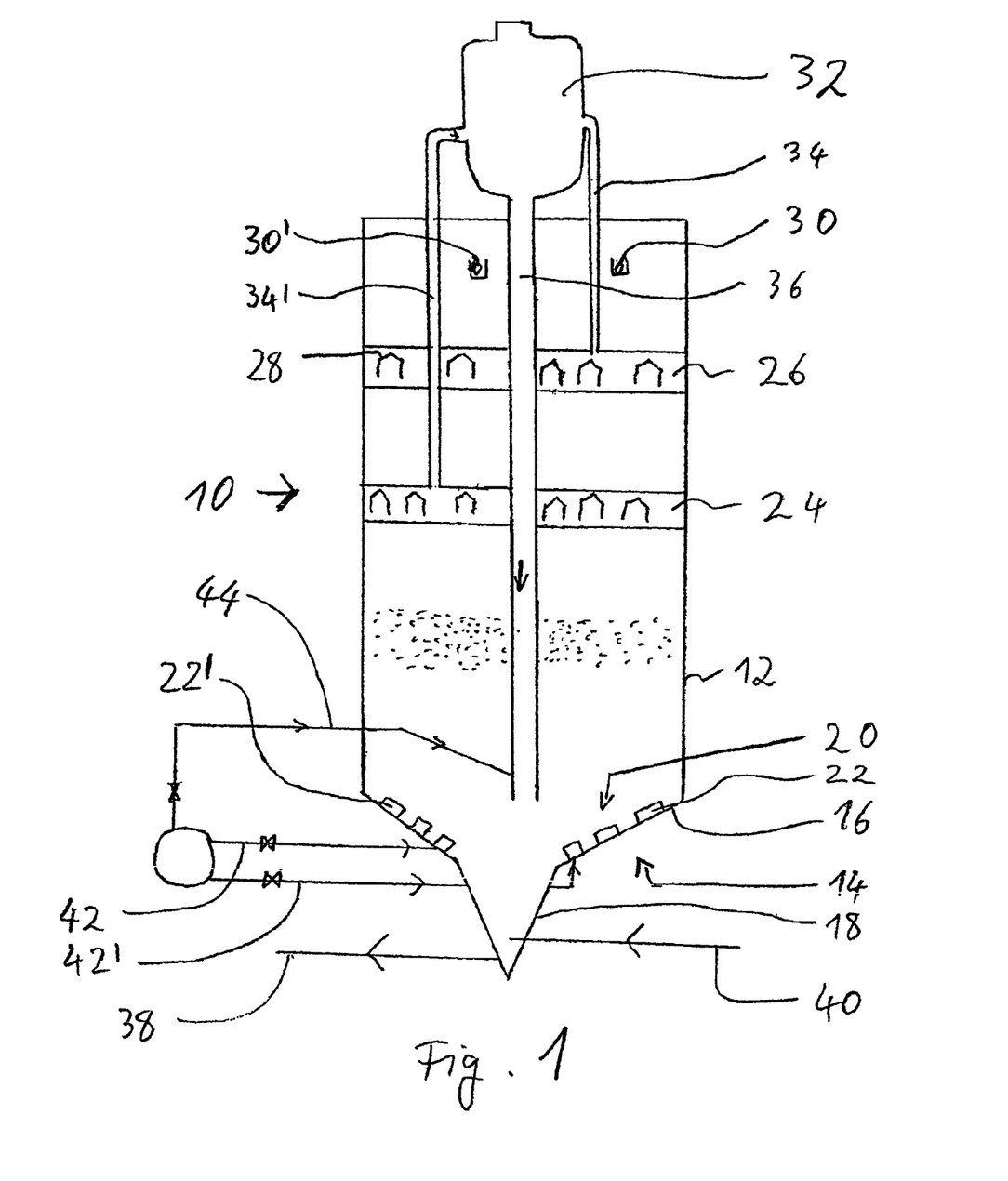
FIG. 1 a schematic longitudinal sectional view of a reactor for the anaerobic treatment of waste water in accordance with a first embodiment of the present invention.

The bioreactor 10 shown schematically in longitudinal section in FIG. 1 includes a reactor tank 12 which is made cylindrical in its middle and upper part and converges downwardly in double cone form in its lower part 14, with the upper part 16 of the double cone having a lower inclination or a smaller angle than the lower part 18 of the double cone with respect to the horizontal plane. An inflow distributor 20 is located at the upper part 16 of the double cone and comprises a plurality of deflection means 22, 22' which are fastened to the inner wall of the reactor tank 12 and which extend from the reactor wall at a specific angle and which cover slots (not shown) provided thereunder in the wall of the reactor tank 12. The inflow distributor 20 can generally also be arranged at the lower part 18 of the double cone or, for example, be fastened via holders remote from the reactor tank wall 12.

Two separators 24, 26, which each comprise a plurality of gas hoods 28, are located in the middle and upper regions of the reactor tank 12. In practice, each of the separators 24, 26 comprises a plurality of layers of gas hoods 28; in the present FIG. 1, however, only one layer of gas hoods 28 each is shown per separator 24, 26 for reasons of simplicity. Alternatively to this, the reactor can also include only one separator 24, 26 instead of two different separators 24, 26. Overflows 30, 30' via which the treated water is drawn off from the reactor 10 are located above the upper separator 26.

A gas separation device 32 is arranged on the reactor 10 and is connected via the lines 34, 34' to the two separators 24, 26. In addition, a sink line 36 leads into the lower part of the reactor 10 from the base of the gas separation device 32.

Furthermore, a drainage line 38 as well as an inflow line 40 are located in the lower part of the reactor 10, namely in the lower part 18 of the double cone, with solids or a suspension of solid and liquid being able to be drawn off out of the reactor 10 via the drainage line 38 and with liquid being able to be introduced via the inflow line 40 for the flushing of the lower reactor tank part 14. Finally, a plurality of inflow lines 42, 42' are provided in the reactor 10 which lead to the individual deflection means 22, 22' of which only some are shown in FIG. 1 for reasons of clarity. In addition, an inflow line 44 is provided in the reactor 10 which opens into the lower end of the sink line 36.

In the operation of the reactor, waste water to be treated is introduced into the reactor tank 12 via the inflow lines 42, 42' through the slots (not shown) in the reactor tank 12 located in the wall of the reactor tank 12 in the upper part 16 of the double cone and is deflected by the deflection means 22, 22' so that the supplied waste water is deflected to a circular flow, viewed from the reactor cross-section. An intimate mixture between the supplied waste water and the medium located in the reactor 10 thereby arises, with said medium comprising waste water which has already been partly treated, microorganism pellets which are indicated by small dots in FIG. 1 and small gas bubbles. The introduced waste water flows slowly upwardly from the inflow distributor 20 in the reactor tank 12 until it moves into the fermentation zone containing microorganism-containing sludge pellets. The microorganisms contained in the pellets primarily decompose the organic impurities contained in the waste water to methane gas and carbon dioxide gas. Gas bubbles arise due to the gases generated, the larger ones of which release from the pellets and bubble through the medium in the form of gas bubbles, whereas small gas bubbles remain stuck to the sludge pellets. Those pellets to which small gas bubbles stick and which therefore have a lower specific weight than the other pellets and the water rise up in the reactor tank 12 until they reach the lower separator 24.

The free gas bubbles are captured in the gas hoods 28 and form a gas cushion beneath the roof of the gas hoods 28. A flotation layer comprising microorganism pellets with small gas bubbles adhering thereto is formed directly beneath the gas cushion. The gas collected in the gas hoods 28 as well as pellets and water from the flotation layer are, for example, drained off via an opening (not shown) present in the end face of the gas hoods 28 out of the gas hoods 28, are optionally mixed with one another via a mixing chamber (not shown) and are guided via the line 34' into the gas separation device 32.

The water, the rising microorganism pellets and the gas bubbles which were not already separated in the lower separator 24 continue to rise upwardly in the reactor tank 12 up to the upper separator 26. Due to the reduction in the hydrostatic pressure between the lower separator 24 and the upper separator 26, the last small gas bubbles are released from the microorganism pellets which have entered into the upper separator 26 so that the specific weight of the pellets increases again and the pellets sink downwardly. The remaining gas bubbles are caught in the gas hoods 28 of the upper separator 26 and are in turn guided into a gas collection line at the end faces of the individual gas hoods 28 from which gas collection line the gas is guided via the line 34 into the gas separator 32. The now treated water continues to rise upwardly from the upper separator 26 until it is drawn off out of the reactor 10 via the overflows 30, 30' and is drained off through a water drainage line (not shown).

The gas is separated from the remaining water and from the microorganism pellets in the gas separator 32, with the suspension of pellets and the waste water being recirculated into the reactor tank part via the sink line 36. In this respect, the outlet opening of the sink line 36 opens at the level of the deflection means 22, 22' where the returned suspension of pellets and waste water is mixed with the waste water supplied to the reactor 10 via the inflow lines 42, 42' and is set into a circular flow, after which the circulation starts again.

Waste water to be treated or fresh water can be supplied continuously or discontinuously to the sink line 36 as required via the inflow line 44 in order to dilute the suspension led back into the reactor 10 through the sink line 36 and thus to prevent a clogging of the sink line 36.

Depending on the origin of the waste water supplied to the reactor 10 via the inflow lines 42, 42', the waste water contains more or fewer solids. Waste water from the paper industry, for example, contains significant concentrations of solid filler materials and lime. After the waste water containing solids has been guided to the slots via the inflow lines 42, 42' and subsequently to the deflection means 22, 22', it is moved via the deflection means 22, 22' into a circular flow with respect to the cross-section of the reactor 10 and, after it has left the deflection means 22, 22', rises upwardly into the cylindrical reactor tank part. The proportion of the solids contained in the waste water which exceeds a minimum degree of specific density already sinks into the double cone converging downwardly after the leaving of the deflection means 22, 22' and is collected in the lower tip of the lower part 18 of the double cone. Some of the lime contained in the waste water furthermore crystallizes at the sludge pellets, which act as crystallization centers in this respect, after the waste water has rise upwardly into the sludge bed zone. Some of the sludge pellets thereby surpass a critical specific weight and consequently sink down from the sludge bed and likewise collect at the lower tip of the lower part 18 of the double cone. It is ensured due to the geometry and to the arrangement of the deflection means 22, 22' that the heavy pellets sinking from the top to the bottom are not deposited on the deflection means 22, 22', but rather slide off from the outer surface of the deflection means 22, 22' and likewise collect in the lower tip of the lower part 18 of the double cone. The sediment collecting at the lower tip of the reactor 10 can, as required, be drawn off out of the reactor 10 continuously or batch-wise via the drainage line 38.

In addition, water can likewise be introduced into the lower part 18 of the double cone continuously or batch-wise as required via the supply line 40 in order to swirl up any sediments adhering to the walls of the double cone, as a result of which these sediments can likewise be drawn off out of the reactor 10 via the drainage lines 38. The water supplied to the reactor 10 via the supply line 40 can be waste water to be treated, recirculated waste water from the reactor, fresh water or a mixture thereof.

Figure 2:
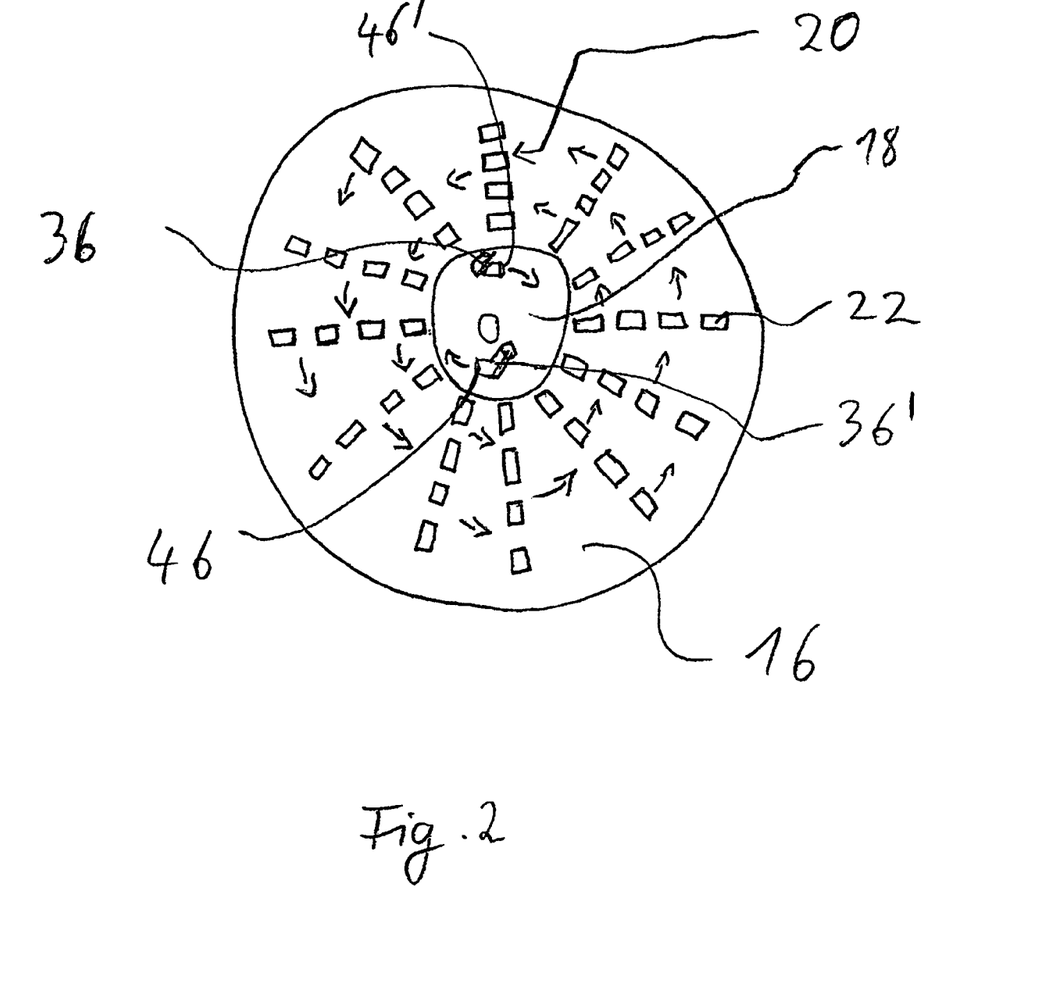
FIG. 2 a schematic plan view of the upper part of a double cone of the lower reactor tank part of a reactor for the anaerobic treatment of waste water in accordance with a second embodiment of the present invention.

The upper part 16 of the double cone of the lower reactor tank part 14 of a reactor for the anaerobic treatment of waste water in accordance with a second embodiment of the present invention is shown in a schematic plan view in FIG. 2. The reactor shown in FIG. 2 corresponds to that shown in FIG. 1 with the exception that the one shown in FIG. 2 includes two sink lines (36, 36').

The inflow distributor 20 includes 36 rectangular deflection means 22 overall, of which a respective 4 are collected together to a row, arranged in the radial direction, of deflection means 22 separated by the reactor tank wall so that the inflow distributor 12 has rows of four respective deflections means 22 each. The two sink lines 36, 36' open into the reactor 10 in the region of the deflection means 22, with the outlet openings 46, 46' of the two sink lines 36, 36' each being arranged in opposite directions tangentially around a circle imagined concentrically around the longitudinal axis of the reactor.

In the embodiment shown in FIG. 2, the individual slots and deflection means are accordingly not distributed surface-proportionally, considered radially outwardly from the longitudinal axis of the reactor. Alternatively to the embodiment shown in FIG. 2, the slots and deflection means can also be distributed surface-proportionally, considered radially outwardly from the longitudinal axis of the reactor. This can preferably be realized in that, as the radial spacing increases, viewed from the longitudinal axis of the reactor, more slots and deflection means are arranged per circular area imagined concentrically around the longitudinal axis of the reactor.

Figure 3:
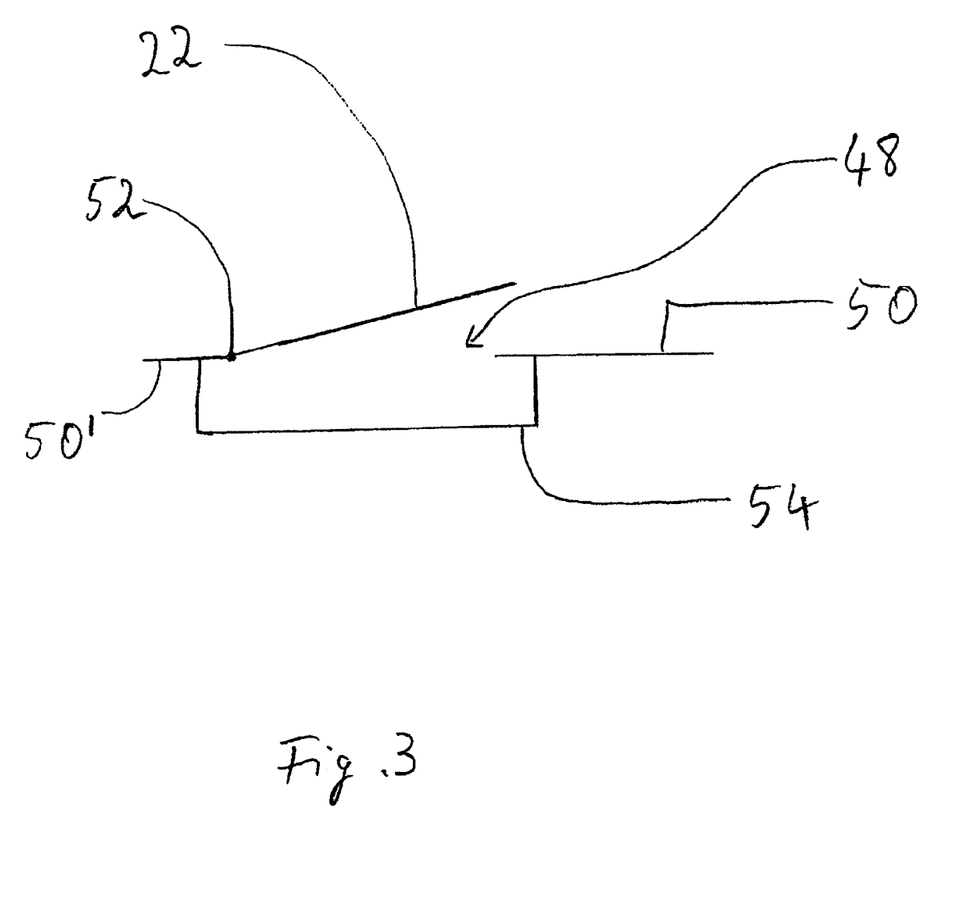
FIG. 3 a longitudinal section of a deflection means in accordance with the embodiments shown in FIGS. 1 and 2.

As can be seen from FIG. 3, which represents a longitudinal section of a deflection means 24 in accordance with the embodiments shown in FIGS. 1 and 2, a rectangular slot 48 is located in the reactor wall 50, 50' of the upper part 16 of the double cone and is surrounded at all sides by the reactor tank wall 50, 50'. A deflection means 22 which is likewise rectangular is rotatably fastened to a side of the slot 48 via a hinge 52 and is adjusted such that it extends at a specific angle from the reactor tank wall 50, 50' and completely covers the slot 48.

A collection line 54 which extends from the inflow line, not shown, radially to the reactor base 50, 50' and is made rectangular in cross-section is located beneath the slot 48 and water is introduced via it into the interior of the reactor through the slot 48 in the operation of the reactor, said water being deflected on the passing of the deflection means 22 into a circular flow, viewed from the reactor cross-section.

Figure 4:
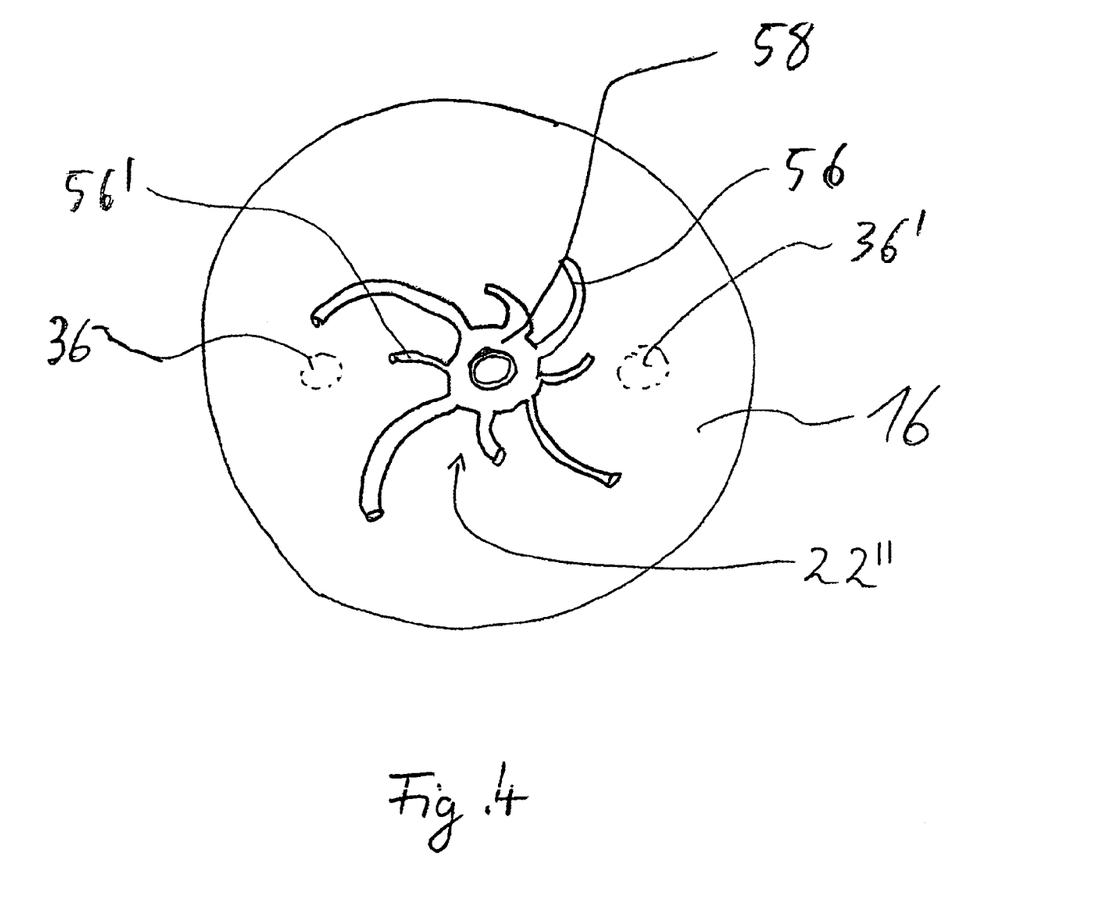
FIG. 4 a schematic plan view of the upper part of the double cone of the lower reactor tank part of a reactor for the anaerobic treatment of waste water in accordance with a third embodiment of the present invention.

In the embodiment shown in FIG. 4, the deflection means 22" provided in the upper part 16 of the double cone of the reactor tank 12 is made as a planar multi-arm spiral which is arranged concentrically around the longitudinal axis of the reactor. The deflection means 22" made as a planar spiral includes eight spiral arms 56, 56' of which four spiral arms 56 have a different length than the remaining four spiral arms 56'. All the spiral arms 56, 56' have a circular cross-section and are made with a substantially semi-elliptical curvature, with the curves of all spiral arms 56, 56' extending in the same direction. A distribution device 58 is located at the center of the spiral deflection means and is connected to an inflow line, not shown, for waste water, with the waste water supplied to the deflection means 22" via this inflow line being distributed to the individual spiral arms 56, 56' via whose outlet openings the waste water enters into the interior of the reactor and is deflected into a circular flow, viewed from the reactor cross-section. The reactor in accordance with this embodiment also includes two sink lines 36, 36'.

Figure 5:
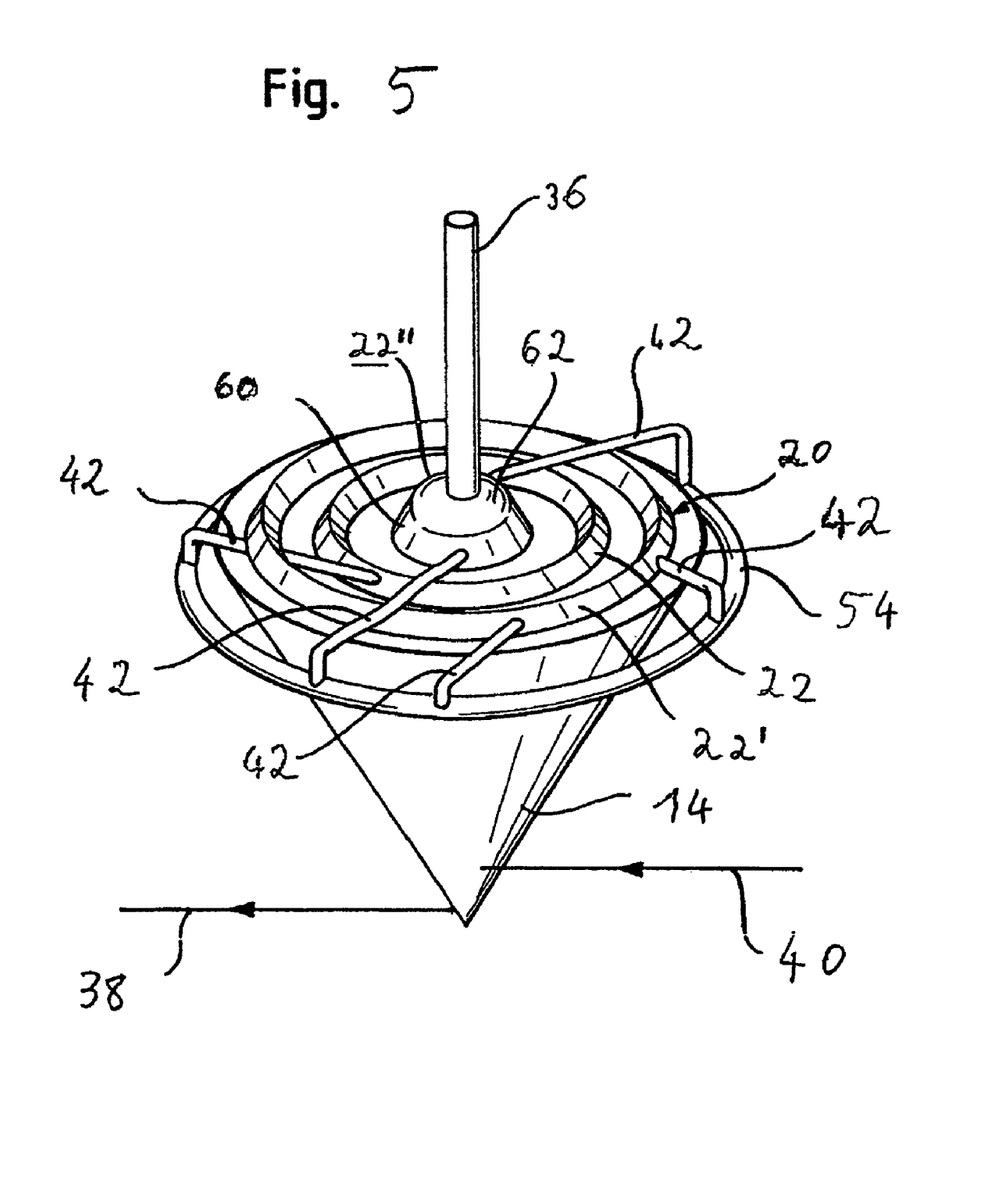
FIG. 5 a perspective view of an inflow distributor contained in the reactor in accordance with the invention in accordance with a further embodiment of the present invention.

An inflow distributor 20 in accordance with a further embodiment which can be used in the reactor 10 in accordance with the invention is shown in FIG. 5. The inflow distributor 20 includes two ring-shaped deflection means 22, 22' which are arranged concentrically around the longitudinal axis of the reactor. The ring bodies of both deflection means 22, 22' have an inversely V-shaped radial section, with the ring bodies being inwardly hollow and downwardly open. In addition, the inflow distributor 20 comprises a hood-shaped deflection means 22" which is arranged concentrically around the longitudinal axis of the reactor and which comprises a hollow truncated cone section 60 in its lower part and a hollow spherical section 62 in its upper part. The hood-shaped deflection means 22" is also inwardly hollow and downwardly, i.e. at the base surface of the hollow truncated cone 60, open.

The inflow distributor 20 is located at the transition between the cylindrical reactor tank 12 (not shown) and the downwardly converging funnel-shaped reactor tank part 14.

Waste water to be treated is introduced in each case into the hollow space of the individual deflection means 22, 22', 22" via the inflow lines 42. All the inflow lines 42 emanate from a central inflow collection line 54 which is circular and is arranged concentrically around the inflow distributor 20.

As can additionally be seen from FIG. 5, the sink line 36 arranged concentrically around the longitudinal axis of the reactor and coming from the gas separation device 32 leads into the hood-shaped deflection means 22", with the outlet opening of the sink line 36 opening just beneath the upper boundary of the deflection means 22". As already stated, a suspension of waste water and microorganism pellets is led back into the region of the inflow distributor 20 via the sink line 36 during reactor operation. To prevent a clogging of the sink line 36 as a result of a high concentration of pellets in the suspension, for example, or as a result of a pressure drop in the sink line 36, a further inflow line (not shown) can open into the sink line 36 above the upper boundary of the hood-shaped deflection means 22" in order to generate a turbulent flow at the opening point in the sink line 36 through which any clogging or pellet agglomerations are eliminated by shearing forces.

Figure 6:
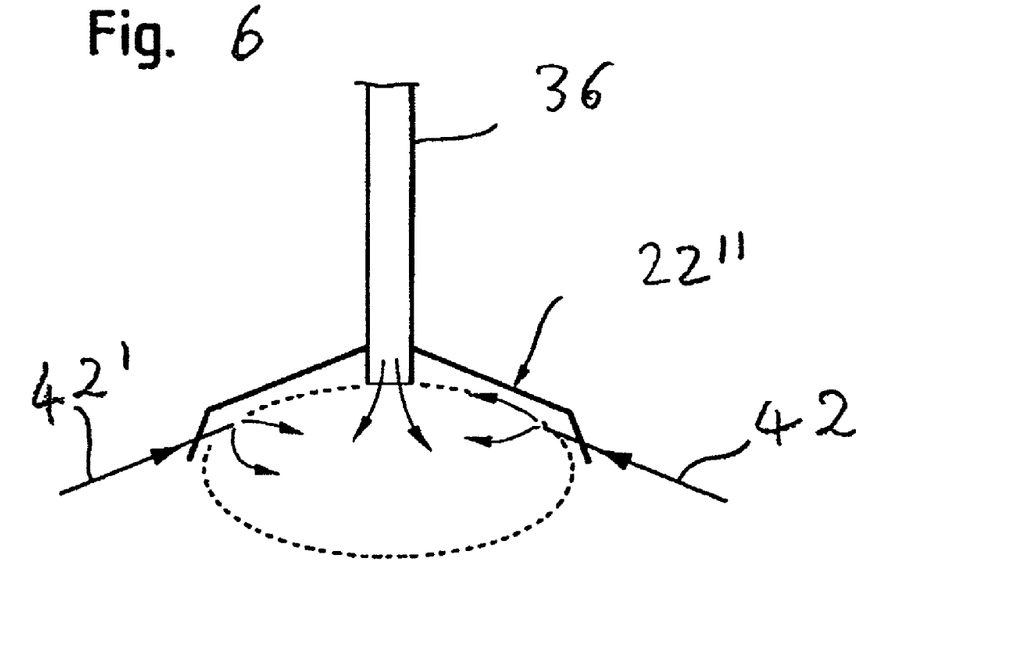
FIG. 6 a schematic radial section of a deflection means arranged in hood-shape concentrically around a sink line; as well as FIG. 7 a schematic radial section of a ring-shaped deflection means arranged concentrically around a sink line.

In FIG. 6, the part of an inflow distributor 20 comprising the lower part of the sink line 36 and the hood-shaped deflection means 22" is shown in schematic radial section which corresponds to the inflow distributor 20 shown in FIG. 5 with the exception that the hood-shaped deflection means 22" has a hollow conical section instead of a hollow spherical section in its upper part. In the operation of the reactor 10, waste water to be treated is introduced into the hollow space of the hood-shaped deflection means 22" via the inflow lines 42, 42'.

Furthermore, a suspension of recirculated waste water and microorganism pellets move via the sink line 36 into the hollow space of the hood-shaped deflection means 22". The flow paths at the outlet openings of the inflow lines 42, 42' and of the sink line 36 are indicated by arrows in FIG. 6. A mixed zone which is indicated by the dotted circle in FIG. 6 and in which suspension of waste water and microorganism pellets emerging from the sink line 36 is mixed intimately together with the waste water to be treated supplied via the inflow lines 42, 42' arises in the hollow space of the hood-shaped deflection means 22" due to the flow relationships.

Figure 7:
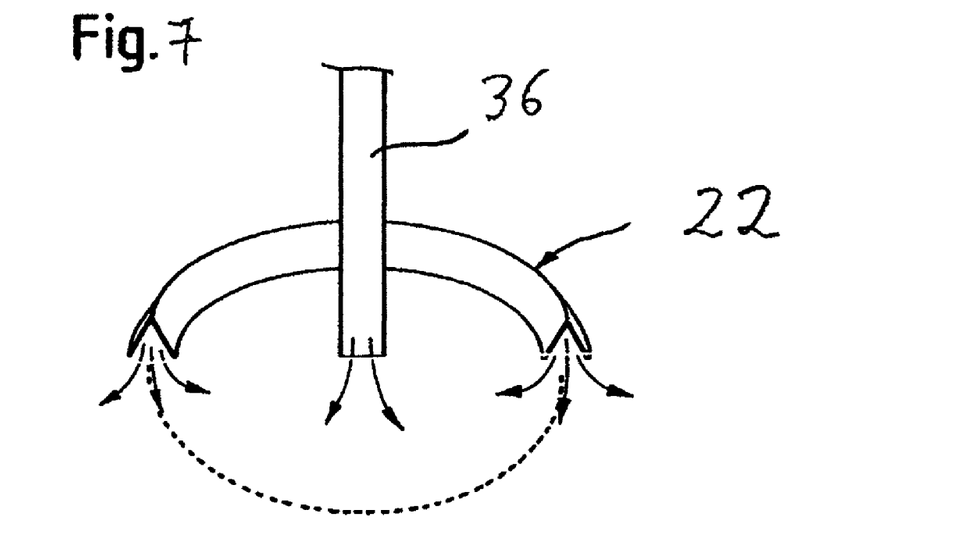

An alternative embodiment to the embodiment of FIG. 6 is shown in FIG. 7. In the embodiment shown in FIG. 7, a ring-shaped deflection means 22 having an inversely V-shaped radial section is arranged concentrically around the sink line 36. The outlet opening of the sink line 36 is located approximately at the level of the lower end of the ring body. The flow relationships of the waste water supplied through the sink line 36 and of the recirculated pellets as well as of the waste water to be treated deflected by the ring-shaped deflection means 22 are also indicated by arrows in this embodiment. A mixing zone also arises in this embodiment which is indicated by dots in FIG. 7 and in which the waste water supplied via the inflow lines 42 (not shown) as well as the waste water recirculated via the sink line 35 and the pellets are mixed intimately with one another.

REFERENCE NUMERAL LIST 10 (bio)reactor
12 reactor tank
14 lower, funnel-shaped reactor tank part
16 upper part of the double cone
18 lower part of the double cone
20 inflow distributor
22, 22', 22" deflection means
24 lower separator
26 upper separator
28 gas hood
30, 30' overflow
32 gas separation device
34, 34' line
36, 36' sink line
38 drainage line
40 supply line for flushing
42, 42' inflow line to the deflection means
44 inflow line to the sink line
46, 46' outlet opening of the sink line
48 slot
50, 50' reactor tank wall
52 hinge
54 collector line
56, 56' spiral arm
58 distribution device
60 hollow truncated cone section
62 hollow spherical section

The invention claimed is:

1. A reactor (10) for the anaerobic treatment of waste water comprising a reactor tank (12), at least one inflow line (42, 42') arranged in the lower region (14) of the reactor tank (12) for the supply of waste water to be treated into the reactor (10), at least one inflow distributor (20) for the mixing of the waste water supplied to the reactor (10) with the medium located in the reactor (10), at least one overflow (30, 30') arranged at the upper region of the reactor tank (12) for the draining off of treated water as well as at least one separator (24, 26), characterized in that
the inflow distributor (20) comprises at least one deflection means (22, 22', 22"), with the at least one deflection means (22, 22' 22") being designed such that waste water emerging from the at least one inflow line (42, 42') is deflected into a circular, upwardly directed flow, viewed from the reactor cross-section, and with 1 to 80% of the reactor cross-section being filled by the at least one deflection means (22, 22', 22").

2. A reactor in accordance with claim 1, characterized in that 2 to 70% of the reactor cross-section is filled by the at least one deflection means (22, 22', 22").

3. A reactor in accordance with claim 2, characterized in that 3 to 60% of the reactor cross-section is filled by the at least one deflection means (22, 22', 22").

4. A reactor in accordance with claim 2, characterized in that 5 to 50% of the reactor cross-section is filled by the at least one deflection means (22, 22', 22").

5. A reactor in accordance with claim 1, characterized in that the at least one inflow line (42, 42') ends outside the reactor tank (12) and at least one slot (48) is provided in the wall of the lower region (14) of the reactor tank (12), with the waste water emerging from the at least one inflow line (42, 42') entering into the lower region (14) of the reactor tank (12) through said at least one slot.

6. A reactor in accordance with claim 5, characterized in that at least one deflection means (22, 22') is provided in the interior of the reactor (10) in the region of the at least one slot (48) and is made such that the waste water entering into the reactor (10) from the at least one slot (48) is deflected into a circular, upwardly deflected flow, viewed from the reactor cross-section.

7. A reactor in accordance with claim 6, characterized in that the at least one deflection means (22, 22') covers the at least one slot (48) at least partly.

8. A reactor in accordance with claim 1, characterized in that the at least one deflection means (22") is made as a planar, multi-arm spiral.

9. A reactor in accordance with claim 8, characterized in that the at least one spiral deflection means (22") has at least two spiral arms (56, 56').

10. A reactor in accordance with claim 8, characterized in that the at least one spiral deflection means (22") has at least four spiral arms (56, 56').

11. A reactor in accordance with claim 8, characterized in that the at least one spiral deflection means (22") has four to eight spiral arms (56, 56').

12. A reactor in accordance with claim 8, characterized in that the individual spiral arms (56, 56') of the at least one spiral deflection means (22") substantially have the shape of a semi-ellipse or of a semi-circle, with the curvature of all the spiral arms (56, 56') extending in the same direction.

13. A reactor in accordance with claim 8, characterized in that the at least one spiral deflection means (22") comprises four to eight substantially semi-elliptical or semi-circular spiral arms (56, 56') of which two to four spiral arms (56) have a different length than the other spiral arms (56').

14. A reactor in accordance with claim 8, characterized in that the reactor has an inflow line (42, 42') and the inflow distributor (20) has a spiral deflection means (22") and a distribution device (58), with the inflow line (42, 42') opening into the distribution device (58) at the center of the one deflection means (22") and the waste water guided by the inflow line being distributed via the distributor (58) to the individual spiral arms (56, 56') of the deflection means (22").

15. A reactor in accordance with claim 1, characterized in that the lower part of the reactor (10) has the shape of a downwardly converging simple cone or double cone.

16. A reactor in accordance with claim 15, characterized in that a drainage line (38) is arranged at the lower end of the cone.

17. A reactor in accordance with claim 15, characterized in that an inflow line (40) is arranged in the lower region of the cone for the flushing of the reactor base.

18. A method for the anaerobic treatment of waste water, wherein waste water to be treated is supplied to a reactor (10) comprising a reactor tank (12), at least one overflow (30, 30') arranged at the upper region of the reactor tank (12) for the draining off of treated water, at least one separator (24, 26), at least one inflow line (42, 42') arranged in the lower region of the reactor tank (12) and having in each case at least one outlet opening for the supply of waste water to be treated into the reactor (10) as well as at least one inflow distributor (20) for the mixing of the waste water supplied to the reactor (10) with the medium located in the reactor, (10), wherein the inflow distributor comprises at least one deflection means (22, 22', 22") by which 1 to 80% of the reactor cross-section is filled, wherein the outlet opening of the at least one inflow line (42, 42') is arranged such that the at least one deflection means (22, 22', 22") is designed and the speed of the supplied waste water is set such that the waste water emerging from the outlet opening of the at least one inflow line (42, 42') is deflected in the inflow distributor (20) into a circular, upwardly directed flow, viewed from the reactor cross-section.

* * * * *